United States Patent [19]

Johnson

[11] Patent Number: 4,744,789
[45] Date of Patent: May 17, 1988

[54] SYRINGE DEVICE FOR BODY FAT INJECTION

[76] Inventor: Gerald W. Johnson, 17070 Red Oak, Suite 301, Houston, Tex. 77090

[21] Appl. No.: 82,798

[22] Filed: Sep. 18, 1987

Related U.S. Application Data

[62] Division of Ser. No. 925,443, Oct. 31, 1986, Pat. No. 4,710,162.

[51] Int. Cl.⁴ ............................................. A61M 5/315
[52] U.S. Cl. .................................... 604/218; 604/223; 128/765
[58] Field of Search ............... 604/187, 218, 223, 232; 222/162, 323, 387; 128/765

[56] References Cited

U.S. PATENT DOCUMENTS

| 3,776,218 | 12/1973 | Svensson | 128/765 |
| 3,973,554 | 8/1976 | Tipton | 604/187 |
| 4,594,073 | 6/1986 | Stine | 128/765 |

FOREIGN PATENT DOCUMENTS 194878  3/1965  Sweden ................. 128/765

Primary Examiner—C. Fred Rosenbaum
Assistant Examiner—J. L. Kruter
Attorney, Agent, or Firm—Neal J. Mosely

[57] ABSTRACT

A body fat injection syringe holder with a mechanism for retracting the barrel of a syringe to the plunger and a mechanism for retracting the plunger simultaneously retracting the plunger with the barrel. A trigger apparatus for variably controlling the rate of retraction of the barrel relative to the retraction of the plunger.

4 Claims, 4 Drawing Sheets

SYRINGE DEVICE FOR BODY FAT INJECTION

This is a continuation of co-pending application Ser. No. 925,443 filed on Oct. 31, 1986 now U.S. Pat. No. 4,710,162.

BACKGROUND OF THE INVENTION

1. Field of the Invention

This invention relates to new and useful improvements in processes and apparatus for reconstructive surgery of the human body and more particularly to a process wherein fat is removed from one part of a body and inserted into an other part, and to apparatus specially constructed to carry out the steps of fat collection and reinjection.

2. Brief Description of the Prior Art

In the prior art of surgical processes, it is known to remove fatty material from sub-dermal regions of the human body. It is also known to inject inert materials, such as silicone, and organic materials, such as collagen, into selected regions of the body in reconstructive surgery. Surgical instruments are also known for carrying out these procedures. The injection of silicone and of collagen both give rise to problems of tissue compatibility and sometimes serious rejection reactions occur.

MacLean U.S. Pat. No. 2,715,899 discloses a suction curette with a valved opening for controlling application of suction.

Jensen U.S. Pat. No. 3,661,144 discloses a suction operated cannula having a storage compartment.

Elmaleh U.S. Pat. No. 3,721,244 discloses a manual suction curettage instrument.

Gram U.S. Pat. No. 3,863,624 discloses a vacuum curettage device with storage.

Shah U.S. Pat. No. 4,340,066 discloses a suction operated endometrial sampling device.

Milgrom U.S. Pat. No. 4,393,879 discloses a tissue collecting apparatus including a vacuum operated curette with storage.

Ishikawa U.S. Pat. No. 3,859,999 discloses a needle assembly incorporating a filter.

Balenderjeet U.S. Pat. No. 4,466,446 discloses a plunger subassembly for blood gas syringes McKinnon U.S. Pat. No. 4,572,210 discloses a syringe with means for allowing passage of air while preventing the passage of blood to obtain a gas-free blood sample.

Ford (Warner-Lambert Company) European Patent Application No. 0,047,176 discloses a syringe with filter for taking blood samples.

McKinnon Canadian Pat. No. 1,170,940 discloses a syringe with means for allowing passage of air while preventing the passage of blood to obtain a gas-free blood sample.

SUMMARY OF THE INVENTION

It is therefore one object of this invention to provide a new and improved process for reconstructing human body surface configurations is disclosed which includes the steps of withdrawing fat from subdermal layers in one portion of the human body and reinjecting the collected fat in other selected body portions in a controlled distribution.

Another object of the invention is to provide an improved collection-injection process for relocating fat in the body utilizing a specially-designed, vacuum-operated, collection syringe including apparatus to wash and filter undesirable particulate and fibrous material from the extracted fat.

Still another object of the invention is to provide an improved collection-injection process for relocating fat in the body utilizing an apparatus for retracting the barrel over the plunger of an injection syringe to retract the needle during injection to distribute the injected fat in a predetermined manner.

Still another object of the invention is to provide an improved collection-injection process for relocating fat in the body utilizing an apparatus for retracting the barrel over the plunger of an injection syringe to retract the needle during injection to distribute the injected fat in a predetermined manner, the apparatus comprising a pistol grip supporting handle, a movable support means for the injection syringe plunger, a mechanism for supporting and moving the injection syringe barrel, separate triggers pivotally connected to the handle and separately movable to operate the movable support and the operating mechanism from the handle.

Another object of the invention is to provide an improved a specially-designed, vacuum-operated, fat collection syringe including apparatus to wash and filter undesirable particulate and fibrous material from the extracted fat.

Still another object of the invention is to provide an improved apparatus for retracting the barrel over the plunger of a fat injection syringe to retract the needle during injection to distribute the injected fat in a predetermined manner.

Still another object of the invention is to provide an improved apparatus for retracting the barrel over the plunger of a fat injection syringe to retract the needle during injection to distribute the injected fat in a predetermined manner, the apparatus comprising a pistol grip supporting handle, a movable support means for the injection syringe plunger, a mechanism for supporting and moving the injection syringe barrel, separate triggers pivotally connected to the handle and separately movable to operate the movable support and the operating mechanism from the handle.

Other objects of the invention will become apparent from time to time throughout the specification and claims as hereinafter related.

The foregoing objects and other objects of the invention are accomplished by a process of reconstructing human body surface configurations is disclosed which includes the steps of withdrawing fat from subdermal layers in one portion of the human body and reinjecting the collected fat in other selected body portions in a controlled distribution. The collection step utilizes a specially-designed, vacuum-operated, collection syringe including apparatus to wash and filter undesirable particulate and fibrous material from the extracted fat. The injection step utilizes a specially designed mechanism for retracting the barrel of a syringe relative to the plunger, mechanism for retracting the plunger simultaneously with the retraction of the barrel, and apparatus for variably controlling the rate of retraction of the barrel relative to the retraction of the plunger. Details of the collection syringe and mechanism for operation of the injection syringe are disclosed.

GENERAL DESCRIPTION OF THE PROCESS

Figure 1:
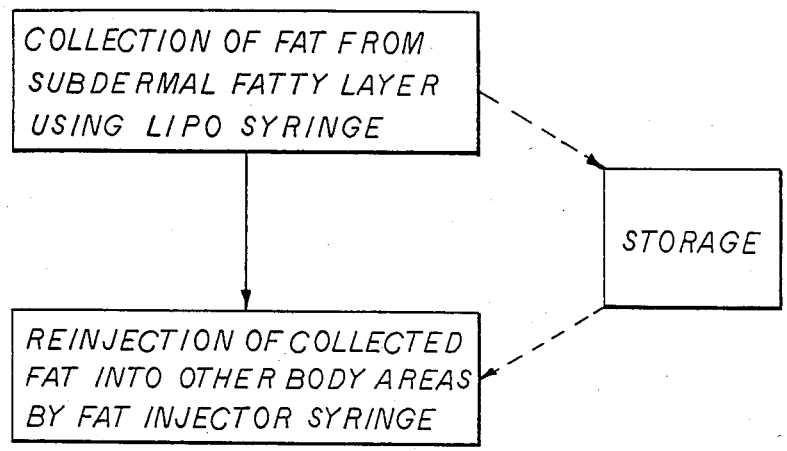
FIG. 1 is a flow diagram of the process comprising this invention.

Referring to FIG. 1 of the drawings, there is shown a flow diagram of this invention which consists of a new and improved process of reconstructing human body surface configurations. In this process, the first step is to withdraw fat from subdermal layers in one portion of the human body utilizing a special lipid processing syringe, hereinafter referred to as a LIPO syringe. The LIPO syring is a specially-designed, vacuum-operated, collection syringe including apparatus to wash and filter undesirable particulate and fibrous material from the extracted fat. The syringe has its needle inserted beneath the skin into a fatty layer and fat is withdrawn under a relatively high vacuum suction and collected in a reservoir where it is washed and filtered before being discharged to storage or directly to an injection syringe.

The collected fat has the advantage that it is compatible with the body tissues when it is used for body reconstruction. The collected fat is reinjected in other selected body portions in a controlled distribution to fill out and expand selected areas of the body. The injection step utilizes a specially designed mechanism for retracting the barrel of the injection syringe relative to its plunger. A mechanism is also provided for retracting the plunger simultaneously with the retraction of the barrel. The rate of retraction of the barrel can be varied relative to the retraction of the plunger. Details of the collection syringe and mechanism for operation of the injection syringe are described below.

DESCRIPTION OF THE COLLECTION SYRINGE

Figures 2, 3:
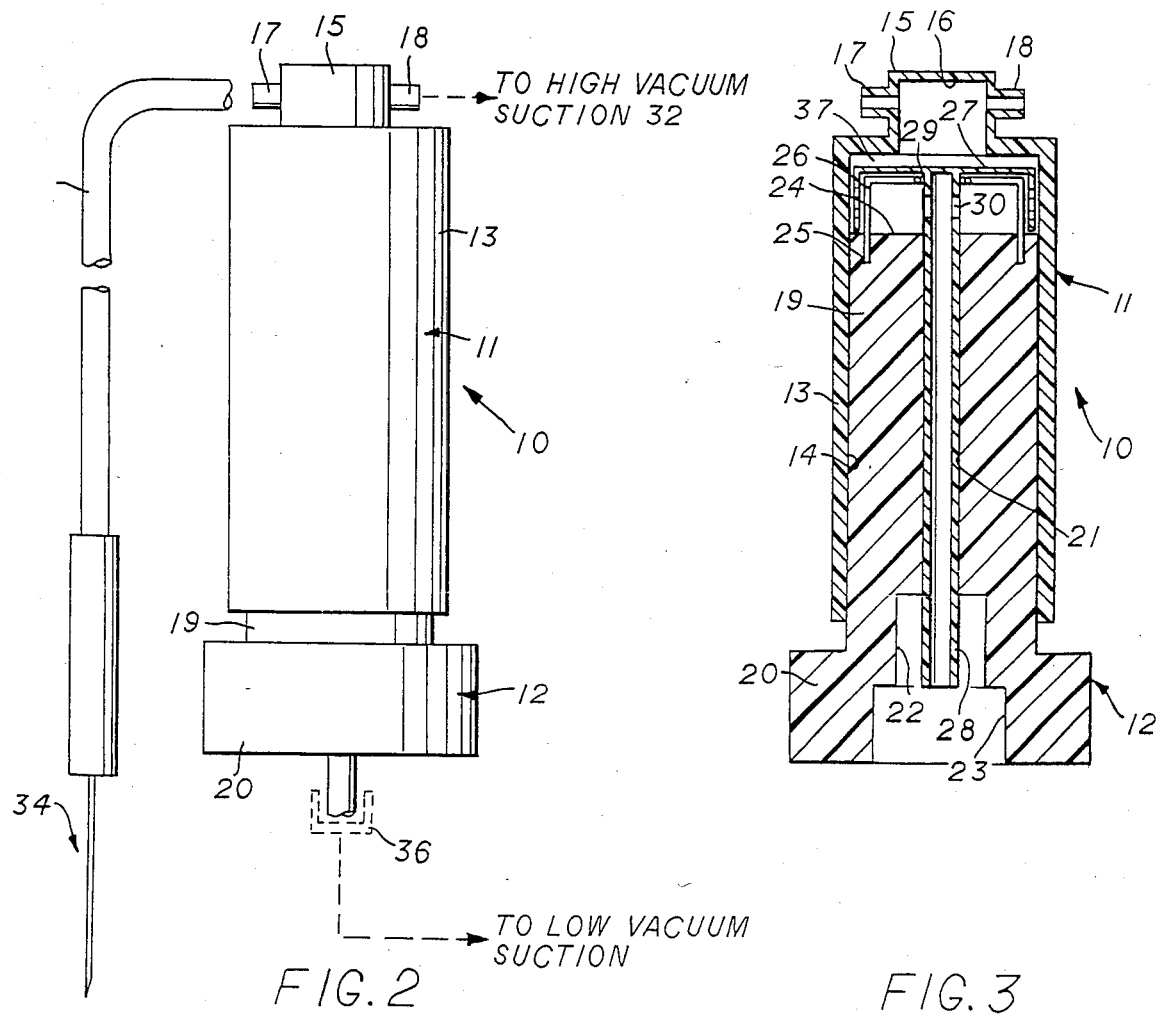
FIG. 2 is a view in elevation of the fat collection syringe used in the process of this invention.
FIG. 3 is a view in longitudinal central section of the syringe shown in FIG. 2.
Figure 4:
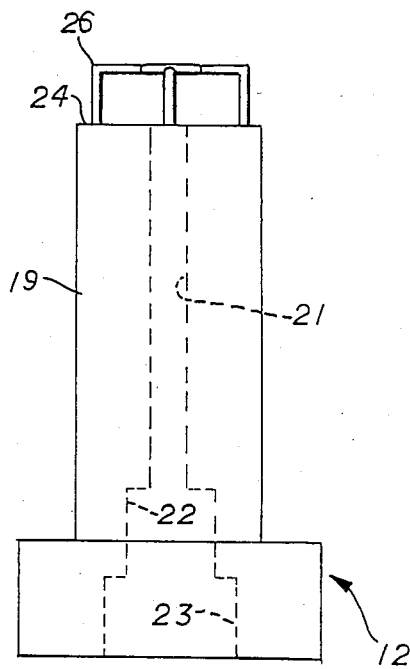
FIG. 4 is a view in elevation of the plunger from the syringe shown in FIGS. 2 and 3.
Figure 5:
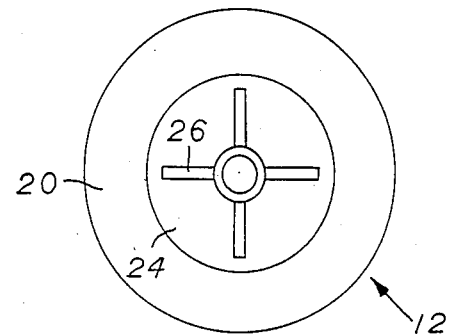
FIG. 5 is a top end view of the plunger from the syringe shown in FIGS. 2 and 3.
Figure 6:
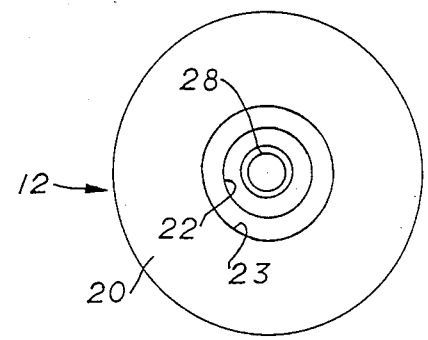
FIG. 6 is a bottom end view of the plunger from the syringe shown in FIGS. 2 and 3.
Figure 7:
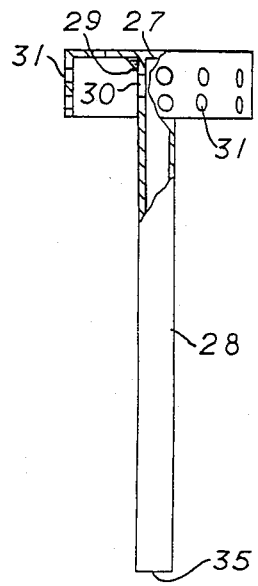
FIG. 7 is a detail view, partially in elevation and partially in section of the suction tube and filter cup from the syringe shown in FIGS. 2 and 3.
Figure 8:
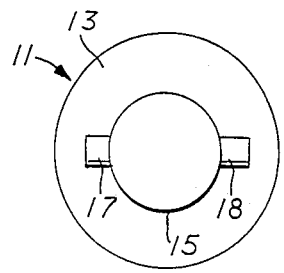
FIG. 8 is a top end view of the barrel from the syringe shown in FIGS. 2 and 3.
Figure 9:
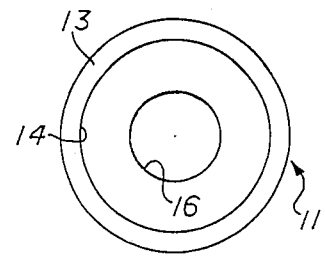
FIG. 9 is a bottom end view of the barrel from the syringe shown in FIGS. 2 and 3.

The lipid processing syringe, or LIPO syringe, is shown in detail in the assembly view of FIG. 2, and in the sectional and detail views of FIGS. 3–9.

LIPO syringe 10 comprises a barrel 11 and movable plunger 12, both preferably of a thermally stable molded thermoplastic or thermosetting material. Barrel 11 has a cylindrical wall 13 and inner cylindrical cavity 14 which slidably receives plunger 12. Barrel 11 has a smaller cylindrical extension 15 with a small cylindrical cavity 16 open to cavity 14. Hollow nipples 17 and 18 open from cavity 16 for connection to vacuum suction on one side and to a fat collection needle on the other side.

Plunger 12 comprises a one-piece molded member having a cylindrical plunger portion 19 and an enlarged cylindrical base or flange portion 20. Passage 21 extends longitudinally through plunger portion 19 and opens into cylindrical openings or counterbores 22 and 23 in base portion 20.

Inner end 24 of plunger portion 19 has a plurality of holes or recesses 25 which receive wire or rod-like prongs 26 which form a scraper for a filter mounted on the plunger. Filter cap 27 is secured on the end of a suction tube 28 by soldering or the like as indicated at 29. Suction tube 28 is hollow for its entire length but is closed off at the end by an imperforate portion of filter cap 27. Holes or apertures 30 open through the wall of suction tube 28 adjacent the filter cap 27. Suction tube 28 is otherwise imperforate. Filter cap 27 has a plurality of spaced holes or apertures 31 for filtering wash liquid and fine material therethrough. Suction tube 28 is longitudinally movable in passage 21 and may be rotated to rotate filter cap 27 to scrape against scraper wires or rods 26.

Nipple 18 is connected initially to a source 32 of high vacuum suction and later in the process to a source of wash liquid. Nipple 17 is initially connected by tubing 33 to collection needle 33, which may be the fat collection needle apparatus shown in Johnson U.S. Pat. No. 4,536,180. The lower end 35 of suction tube 28 is closed by a cap 36 initially but is connected, later in the process, to a source of low vacuum suction for drawing a wash liquid through the fat collected in the chamber or reservoir 37 formed by retraction of plunger portion 19 in cavity 14. The operation of this collection syringe or LIPO syringe will be described more fully below.

DESCRIPTION OF THE INJECTION SYRINGE OPERATING DEVICE

Figure 10A:
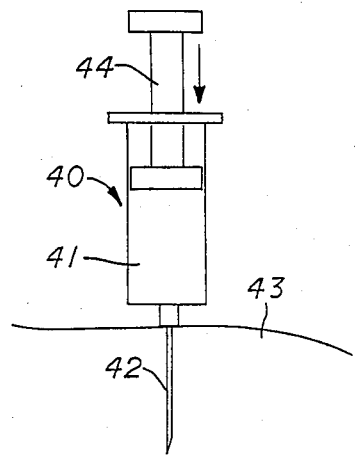
FIG. 10A is a schematic view showing the operation of a syringe on insertion into body tissue.
Figure 10B:
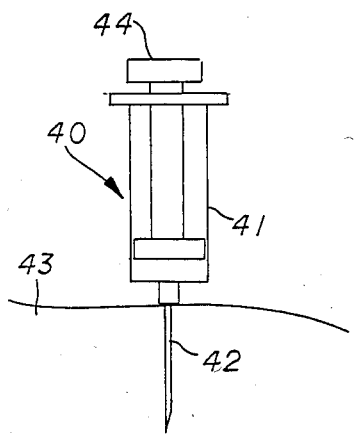
FIG. 10B is a schematic view showing the operation of a syringe on insertion into body tissue with the plunger moved into the barrel of the syringe.

In the operation of syringes for injecting medication or other materials into the body the commonly used technique is that shown in FIGS. 10A and 10B of the drawings. There is shown a syringe 40 having a barrel 41 and needle 42. The needle 42 is shown in a position fully injected into the body 43. Plunger 44 is shown in an initially retracted position with the barrel full of the material to be injected. The plunger 44 is slowly moved to a fully inserted position while maintaining the needle 42 in a fixed location as in FIG. 10B. This technique is used where a fixed quantity of material is to be injected into a single location.

Figure 11A:
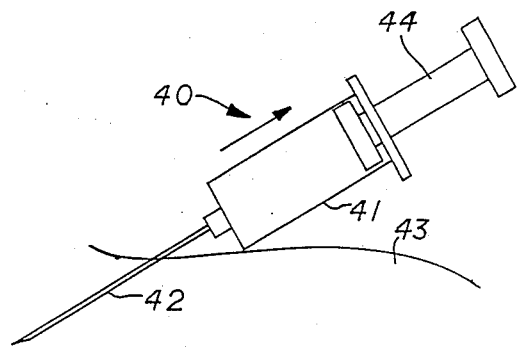
FIG. 11A is a schematic view showing the operation of a syringe on insertion into body tissue when operated to distribute the injected material by withdrawing the needle as the syringe is operated.
Figure 11B:
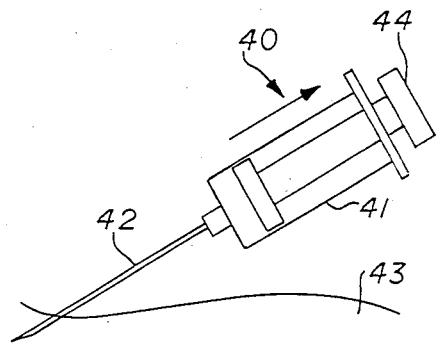
FIG. 11B is a schematic view showing the operation of the syringe shown in FIG. 11A with the barrel retracted over the plunger to inject material while simultaneously withdrawing the needle.

Another technique for operation of a syringe is that shown in FIGS. 11A and 11B. This is used where it is necessary to change the point of application of the injected material while the material is being injected. For example, when injecting a local anesthetic it may be desirable to distribute the injected material over a region rather than have it concentrated at a single point. In FIG. 11A, the syringe 40 is shown with the needle 42 fully injected. In this technique, the plunger 44 is held in a fixed position and the barrel 41 is retracted. This causes the material in barrel 41 to be injected while needle 42 is slowly withdrawn as seen in FIG. 11B. The material being injected is thus injected along the length of the needle 42 as it is withdrawn rather than being concentrated at the tip of the needle as in the technique shown in FIGS. 10A and 10B. In some cases, the plunger 44 may be moved while the barrel 41 is being retracted which permits the distribution of injected material to be varied. This technique is especially useful when used in injecting fat into selected body regions in accordance with this invention.

The manipulation of a syringe according to the procedure described above and shown in FIGS. 11A and 11B is difficult to do in a regular and controlled manner by hand. This is especially true when simultaneous retraction of the barrel 41 and plunger 44 is required. The present invention of an injection gun for manipulating a syringe as just described overcomes the difficulties of the manual technique.

Figure 12:
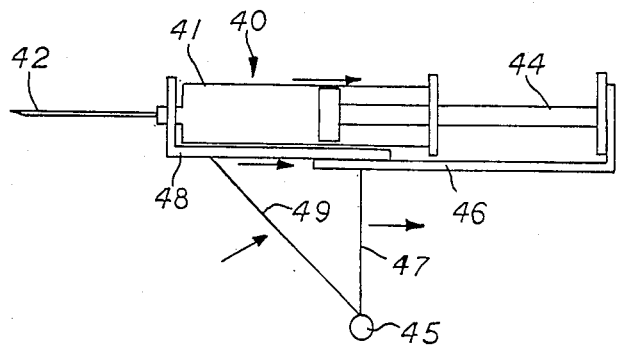
FIG. 12 is a schematic view of an apparatus for supporting a syringe for moving the barrel back over the plunger to inject material while simultaneously withdrawing the needle and providing means to move the plunger simultaneously to vary the distribution of the material being injected.

In FIG. 12, there is shown a schematic of the mechanical elements required in an injection apparatus for controlled manipulation of a syringe. A supporting member 45 supports movable member 46 which receives and supports plunger 44 of syringe 40. Movable member 46 is connected by operating member 47 to supporting member 45. A second supporting member 48 receives and supports the barrel 41 of syringe 40 for movement relative to plunger 44. Supporting member 48 is connected by operating member 49 to supporting member 45. Controlled movement of operating members 47 and 49 will cause member 48 to retract barrel 41 over plunger 44, and where needed, to move the support for plunger 44 to vary the rate of injection of material while varying the point of application of the injected material.

Figure 13:
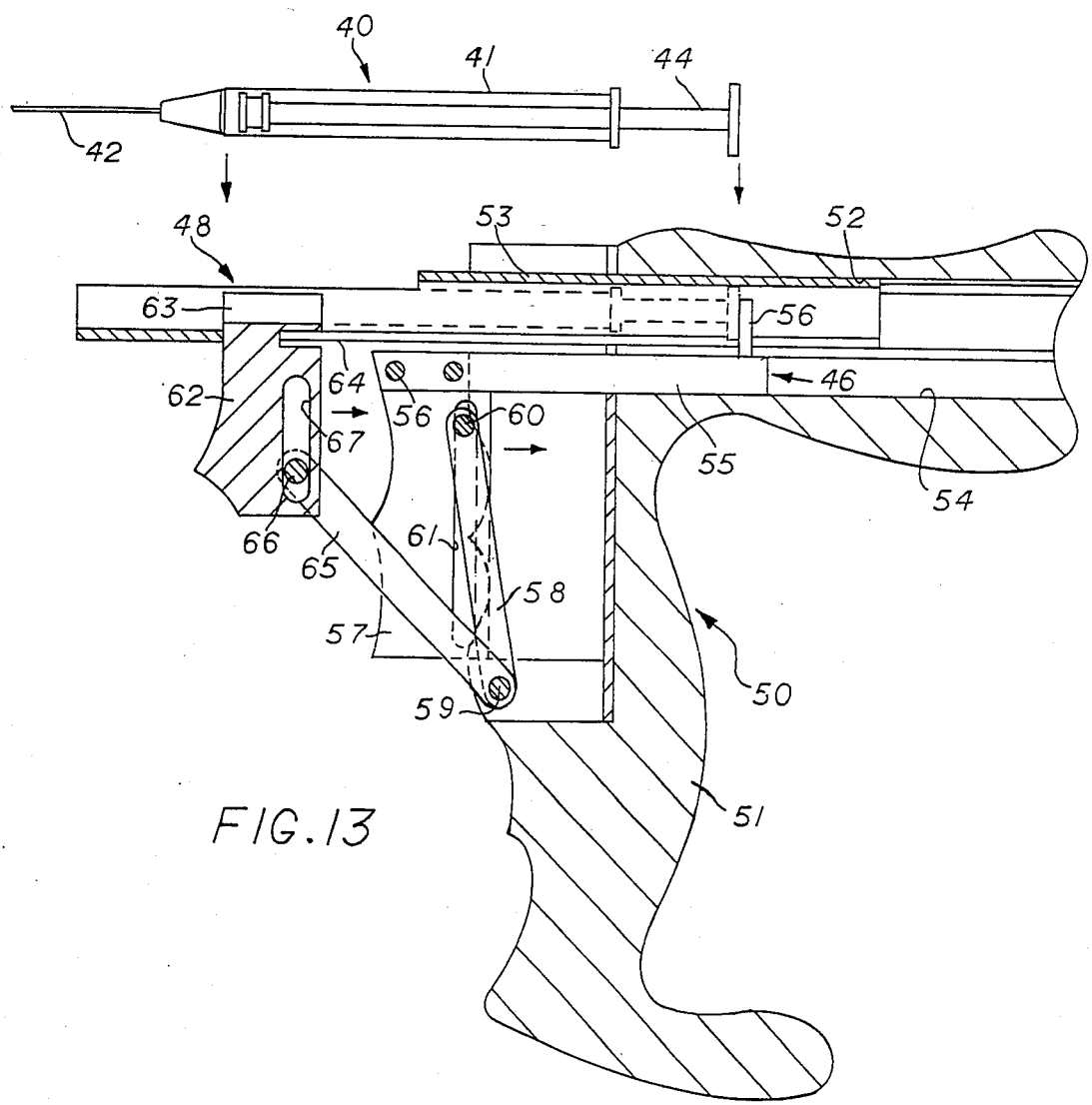
FIG. 13 is a view in side elevation of an apparatus for operating a syringe according to the mode of operation of the apparatus shown schematically in FIG. 12.

In FIG. 13, the syringe operating apparatus is shown as an injection gun 50 with syringe 40 positioned above it in preparation for insertion into the gun. Injection gun 50 has a handle 51 with a longitudinal passage 52 in which there is positioned a supporting and guiding sleeve 53. Handle 51 has another passage 54 which receives supporting member 46 consisting of sliding rod 55 and abutment pin 56 against which the syringe plunger 44 is positioned. Rod 55 is secured by screws or rivets 56 to trigger 57. A link 58 is connected at one end to a pivot 59 on handle 51 and at the other end to pin 60 which rides in slot 61 in trigger 57. Movement of trigger 57 provides a controlled movement of supporting member 46 to control the movement of plunger 44 backward.

Supporting member 48, for retracting barrel 41 of syringe 40 over plunger 44, comprises trigger 62 having a spring clip portion 63 at its upper end for receiving and moving syringe barrel 41. Clip portion 63 of trigger 62 is guided for movement in slot 64 of guide sleeve 53. Link 65 is connected at one end to pivot 59 on handle 51 and at the other end to pin 66 which rides in slot 67 in trigger 62. Movement of trigger 62 provides a controlled movement of supporting member 48 to control the retracting movement of barrel 41 over plunger 44.

DETAILED DESCRIPTION OF OPERATION OF THE PROCESS AND APPARATUS

As described above, this invention consists of a new and improved process of reconstructing human body surface configurations. In this process, the first step is to withdraw fat from subdermal layers in one portion of the human body utilizing a special lipid processing syringe, hereinafter referred to as a LIPO syringe 10. The LIPO syringe 10 is a specially-designed, vacuum-operated, collection syringe including apparatus to wash and filter undesirable particulate and fibrous material from the extracted fat. LIPO syringe 10 is provided to the user in a sterile package for use under sterile conditions, as in an operating room, or using sterile gloves, as in a clinic.

Syringe 10 has needle 34 inserted beneath the skin into a fatty layer and nipple 18 is initially connected to a relatively high vacuum suction 32. Fat is withdrawn under vacuum and collected in reservoir 37 formed by withdrawal of plunger 12 from barrel 11 of LIPO syringe 10. During this phase of the procedure, suction tube 28 is closed by cap 36.

When a sufficient amount of fat has been collected, nipple 18 is disconnected from high vacuum suction 32 and is connected to a source of sterile wash liquid, not shown. The sterile wash liquid may be a sterile saline solution or other suitable medically acceptable liquid (irrigating solution) for washing the collected fat.

The LIPO syringe 10 is then inverted one or more times to wash the fat. When the LIPO syringe 10 is returned to an upright position, as in FIGS. 2 and 3, and allowed to set for a short time, the fat floats to the top of the washing liquid and waste material settles out on the filter cap 27. Application of low vacuum suction through suction tube 28 draws the washing liquid and waste particulate and fibrous material through the small holes 31 in filter cap 27.

Because fat clogs any filter system easily and rapidly, the manner in which the filter is manipulated is important. The filter cap 27 may be moved reciprocally by movement of suction tube 28. Also, filter cap 27 may be rotated to scrape against scraper wires or rods 26 to assist in dislodging the contaminant materials. Repeated extension and retraction of the filter cap and rotation against the scraper wires or rods allow for additional removal of waste solution and contaminants.

A cap is places over nipple 18 on the ned of barrel 11 and nipple 17 is connected by an adapter tube to an injection syringe. Alternatively, the adapter tube may be connected to a storage container to receive the collected fat for storage prior to use. The fat is transferred to fill the injector syringe 40, either directly from the LIPO syringe 10 or from storage. As previously noted, the collected fat has the advantage that it is compatible with the body tissues when it is used for body reconstruction. The collected fat is reinjected in other selected body portions in a controlled distribution to fill out and expand selected areas of the body.

The injection step utilizes a specially designed mechanism, as described above and shown in FIGS. 12 and 13, for retracting the barrel of the injection syringe relative to its plunger. Operating mechanisms 47 and 48 provide for retracting the plunger simultaneously with the retraction of the barrel. The rate of retraction of the barrel can be varied relative to the retraction of the plunger.

Injector syringe 40 (called the LIPOJECT syringe) is placed in injection gun 50 with plunger 44 positioned against the retractable stop 46 and barrel 44 securely held in the spring clip 63 of supporting mechanism 48. Triggers 57 and 62 provide for independent movement of the plunger stop 46 spring clip 63 moving the barrel 41. Independent movement of triggers 57 and 62 can retract barrel 41 over plunger 44 to distribute the injected fat by withdrawing needle 42 during injection and can retract plunger stop 46 to control the rate of injection of fat while needle 42 is being withdrawn.

While this invention has been described fully and completely with special emphasis on certain preferred embodiments, it should be understood that within the scope of the appended claims this invention may be practiced otherwise than as specifically described herein.

I claim:

1. A body fat infection device for operating an injection syringe comprising a barrel with an open end and a closed end with an opening therefrom and a needle supported on said opening, and a plunger movable in said barrel for injecting material into a body in a controlled distribution comprising
    supporting means for said injection syringe plunger,
    operating means for supporting and moving said injection syringe barrel, and
    means for moving said operating means relative to said supporting means to withdraw said needle and injection syringe barrel relative to said injection syringe plunger to inject material from said barrel in a controlled distribution.

2. An apparatus according to claim 1 including
    means to move said injection syringe plunger while said injection syringe barrel and needle are withdrawn in relation thereto.

3. An apparatus according to claim 1 including
    a supporting handle,
    movable supporting means for said injection syringe plunger, and
    operating means for supporting and moving said injection syringe barrel,
    said movable supporting means and said operating means being operated from said handle.

4. An apparatus according to claim 1 including
    a pistol grip supporting handle,
    movable supporting means for said injection syringe plunger,
    operating means for supporting and moving said injection syringe barrel,
    separate trigger means pivotally connected to said handle and separately movable to operate said movable supporting means and said operating means from said handle.

* * * * *